United States Patent [19]
Nelson

[11] Patent Number: 6,013,051
[45] Date of Patent: Jan. 11, 2000

[54] FILTERED ACCESS PORT WITH FILTER BYPASS FOR ACCESSING BODY FLUID SAMPLES

[75] Inventor: Timothy S. Nelson, Chemin Des Esserts, Switzerland

[73] Assignee: Medtronic, Inc., Minneapolis, Minn.

[21] Appl. No.: 09/177,155

[22] Filed: Oct. 22, 1998

[51] Int. Cl.$^7$ .................................................. A61M 11/00
[52] U.S. Cl. ............................................ 604/93; 604/247
[58] Field of Search .......................... 604/30, 93, 246, 604/247

[56] References Cited

U.S. PATENT DOCUMENTS

| | | | |
|---|---|---|---|
| 4,904,237 | 2/1990 | Janese | 604/28 |
| 5,396,899 | 3/1995 | Strittmatter | 128/763 |
| 5,643,207 | 7/1997 | Rise | 604/93 |
| 5,695,490 | 12/1997 | Flaherty et al. | 604/891.1 |
| 5,702,363 | 12/1997 | Flaherty | 604/93 |
| 5,711,316 | 1/1998 | Elsberry et al. | 128/898 |
| 5,713,858 | 2/1998 | Heruth et al. | 604/93 |
| 5,735,814 | 4/1998 | Elsberry et al. | 604/43 |
| 5,738,650 | 4/1998 | Gregg | 604/51 |
| 5,752,930 | 5/1998 | Rise et al. | 604/53 |
| 5,814,014 | 9/1998 | Elsberry et al. | 604/43 |
| 5,832,932 | 11/1998 | Elsberry et al. | 128/898 |
| 5,840,063 | 11/1998 | Flaherty | 604/93 |
| 5,897,528 | 4/1999 | Schultz | 604/49 |

*Primary Examiner*—Wynn Wood Coggins
*Assistant Examiner*—Deborah Blyveis
*Attorney, Agent, or Firm*—Curtis D. Kinghorn; Harold R. Patton

[57] ABSTRACT

An access port is described that allows for filtered introduction of a drug while also allowing bypass of the filter when taking CSF samples. The access port is in fluid communication with a catheter that is surgically implanted in a patient's brain or intraspinal space. The access port has a first chamber in fluid communication with the catheter through a bioretentive filter and a one-way valve. The one-way valve allows fluid to flow only in the direction from the first chamber to the catheter. The bioretentive filter filters the fluid to remove particulate matter, bacteria or other undesirable objects prior to introduction of the fluid to the CSF. The access port also includes a second chamber that is in fluid communication with the catheter. The second chamber is separated from the first chamber by a needle screen and a septum. There is no bioretentive filter or one-way valve on the fluid path between the second chamber and the catheter allowing CSF samples to be taken from the patient in an unfiltered manner from the same device. The needle screen has a hole size that allows only needles smaller than a certain size to pass through.

26 Claims, 8 Drawing Sheets

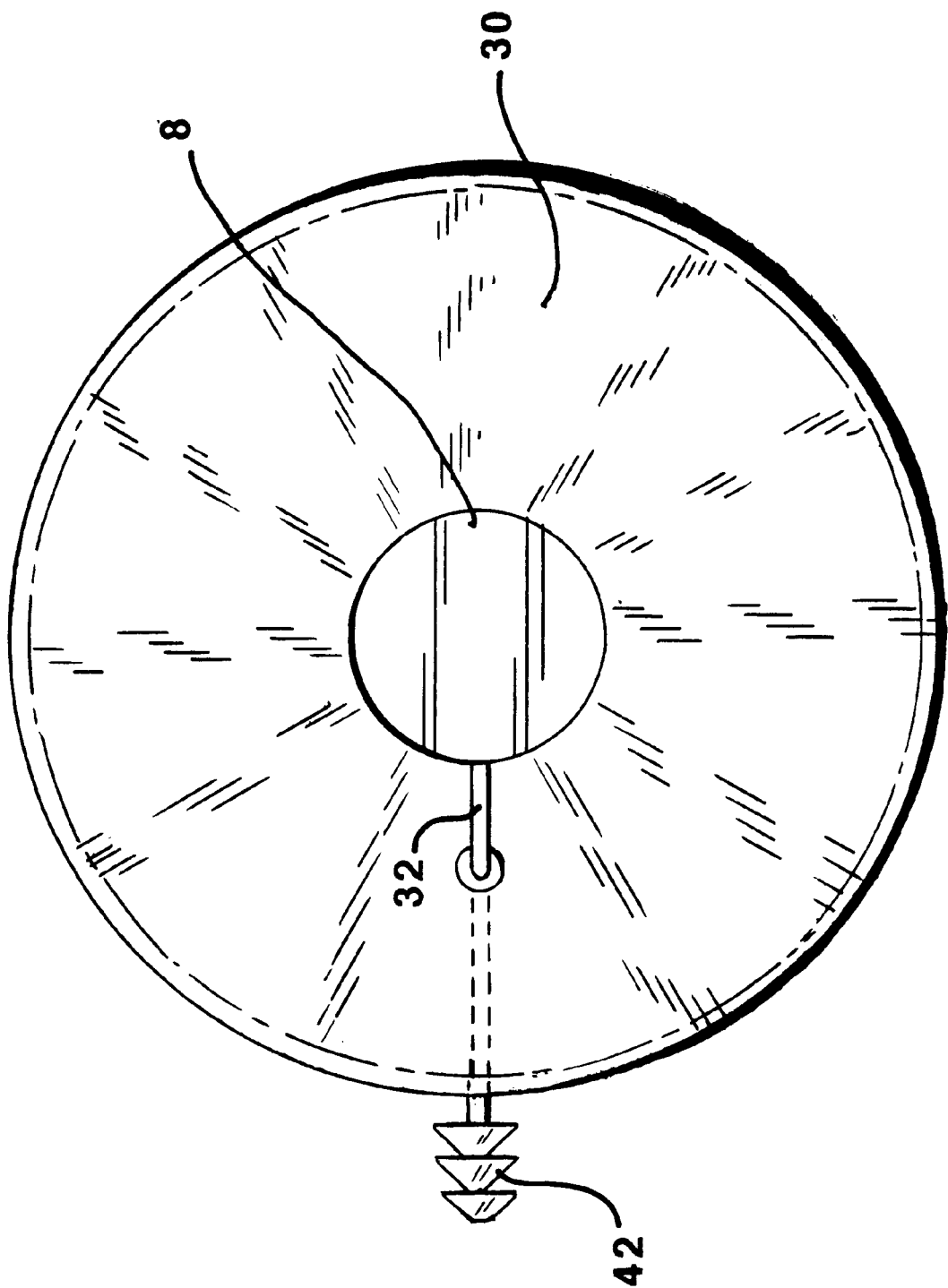

FILTERED ACCESS PORT WITH FILTER BYPASS FOR ACCESSING BODY FLUID SAMPLES

BACKGROUND OF THE INVENTION

1. Field of the Invention

This invention relates generally to medical devices that are implantable in the human body and more particularly relates to a subcutaneously implantable direct delivery access port capable of delivering filtered drugs to the ventricles of the brain or to the intraspinal area and, from the same device, allowing the removal of unfiltered cerebrospinal fluid from the brain or spinal area

2. Description of Related Art

It is often desirable for a physician or other health care professional to withdraw cerebrospinal fluid (CSF) from a patient in order to assess the condition of the CSF or to administer drug to the CSF. Access ports, such as the model 8506 ICV Access Port and the 8507 Intraspinal Port, developed by Medtronic, Inc. of Minneapolis, Minn., allow the physician or other healthcare professional to intermittently withdraw CSF from the ventricles of a patient's brain or intraspinal space or administer drug to the CSF.

These access ports are typically placed cranially or over the ribs and are connected to a catheter which is surgically placed in the intraventricular space of the brain or intraspinal area of the spinal cord. Physicians often require the ability to take CSF samples through the port to confirm port and catheter patency prior to injecting drugs or for evaluation purposes. CSF is withdrawn by inserting a needle through the patient's skin and through a septum that forms the top of the port. The end of the needle is located in the port and CSF is withdrawn from the patient through the catheter and port.

When it is desirable to administer drug to the CSF, a needle is inserted through the patient's skin, through the septum and into the port which is connected to a catheter. The drug is passed into the port where it passes through the catheter into the patient's CSF.

These and other similar products may represent an infection risk to the patient because the drugs are introduced across the blood brain barrier to the neuraxis without first passing through a bioretentive filter in the port. If a filter is placed across the fluid path, it is believed that taking repeated CSF samples through the filter will cause the filter to clog. As the filter becomes clogged, it becomes more difficult if not impossible to either take further CSF samples or administer drugs to the patient through the port. This is a problem in need of a solution.

SUMMARY OF THE INVENTION

When introducing a fluid to the CSF by bypassing the blood-brain barrier, for example via an implanted port and intrathecal catheter, it is often desirable to pass this fluid through a bacterioretentive filter to minimize the risk of infection while simultaneously maximizing the integrity of the body's blood-brain barrier. Bacterioretentive pre-filters are placed on syringes used to introduce drugs to the CSF via implanted ports and catheters. Bacterioretentive filters are also desirable as an integral part of the port itself, reducing the risk of an infection that may result from passing the syringe needle through the skin and introducing potential infection to the system due to this puncture of the skin post filter.

Ports are also used to remove CSF samples from the CNS. These CSF samples may be removed to perform analysis on CSF protein levels, potential CSF infections, cell counts, etc. When collecting such samples, it is not desirable to pass the sample through a bacterioretentive filter as the filter will remove from the sample exactly those items (cell counts, proteins, etc.) desired to be collected by the sample. For this reason, filterless ports are necessary to remove CSF samples.

It is the intent of the present embodiment to achieve both needs (bacterioretentive filtered fluid delivery to the CSF and unfiltered CSF removal) via a single device.

An access port is described that allows for filtered introduction of a drug while allowing bypass of the filter when taking CSF samples. The access port is in fluid communication with a catheter that is surgically implanted in a patient's brain or intraspinal space. The access port has a first chamber in fluid communication with the catheter through a bioretentive filter and a one-way valve. The one-way valve allows fluid to flow only in the direction from the first chamber to the catheter. The bioretentive filter filters the fluid to remove particulate matter, bacteria or other undesirable objects.

The access port also includes a second chamber that is in fluid communication with the catheter. The second chamber is separated from the first chamber by a needle screen and a septum. There is no bioretentive filter or one-way valve on the fluid path between the second chamber and the catheter.

The needle screen has a hole size that allows only needles smaller than a certain size to pass through. In this way, a first needle having a size larger than the size that will pass through the needle screen is used to inject drug into the first chamber. The needle screen prevents the first needle from being able to pass into the second chamber. The septum between the first and second chamber fluidly isolates the second chamber from the first chamber.

To administer a drug, drug is loaded into a syringe having a needle with a diameter larger than the holes in the needle screen. The needle is inserted into the first chamber where the drug is discharged. The drug passes out of the first chamber, through the bioretentive filter and one-way valve to the catheter where it is administered to the patient.

To withdraw CSF, a syringe having a needle with a diameter smaller than the hole size in the needle screen is used. The needle is passed through the first chamber, through the needle screen, through the septum isolating the first and second chambers and into the second chamber. CSF fluid is withdrawn through the needle.

BRIEF DESCRIPTION OF THE DRAWINGS

FIG. 3 is a top view of the access port of the present invention.

DETAILED DESCRIPTION OF THE INVENTION

Figure 1:
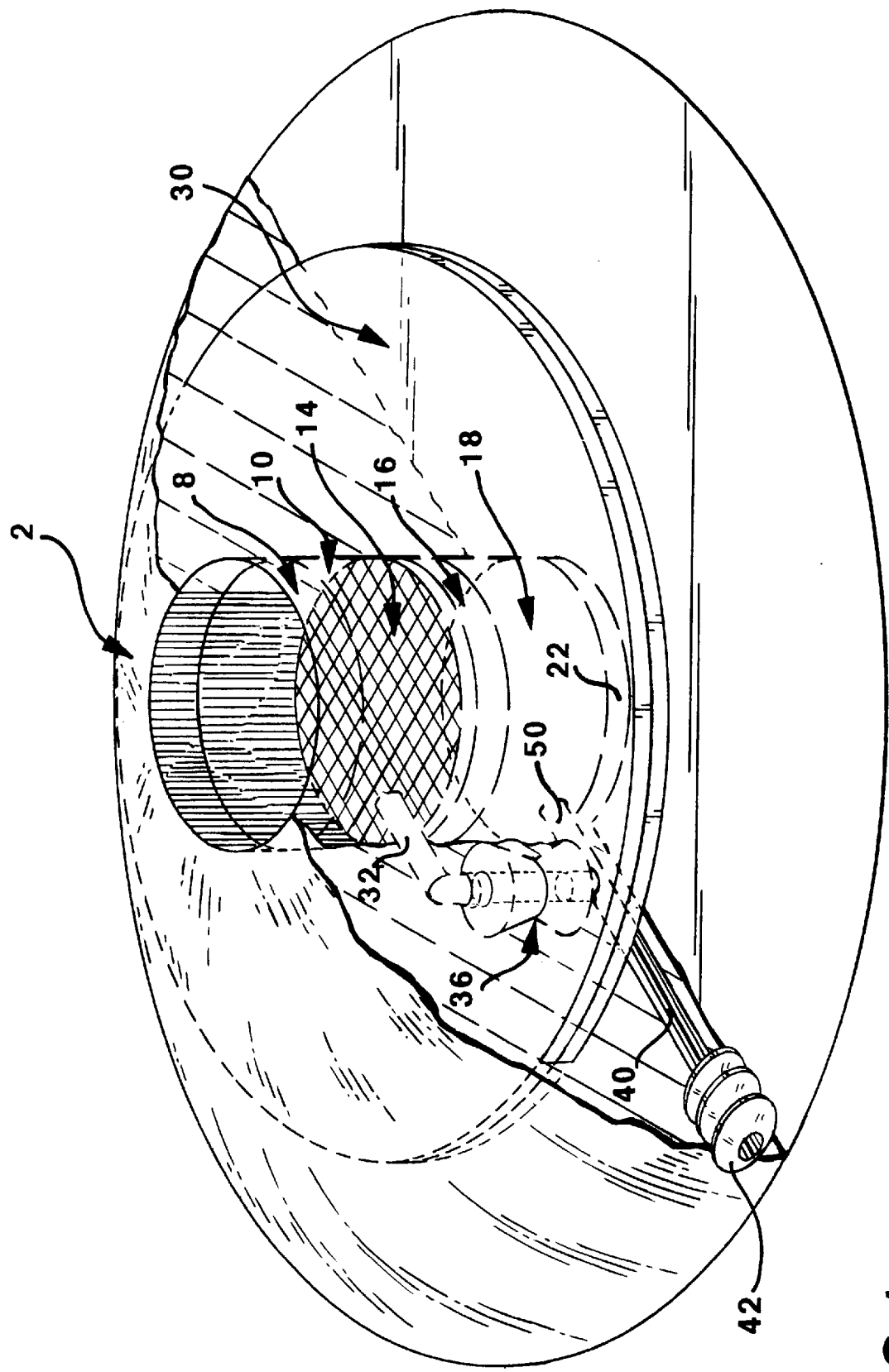
FIG. 1 is a perspective phantom view of the access port of the present invention.
Figure 2:
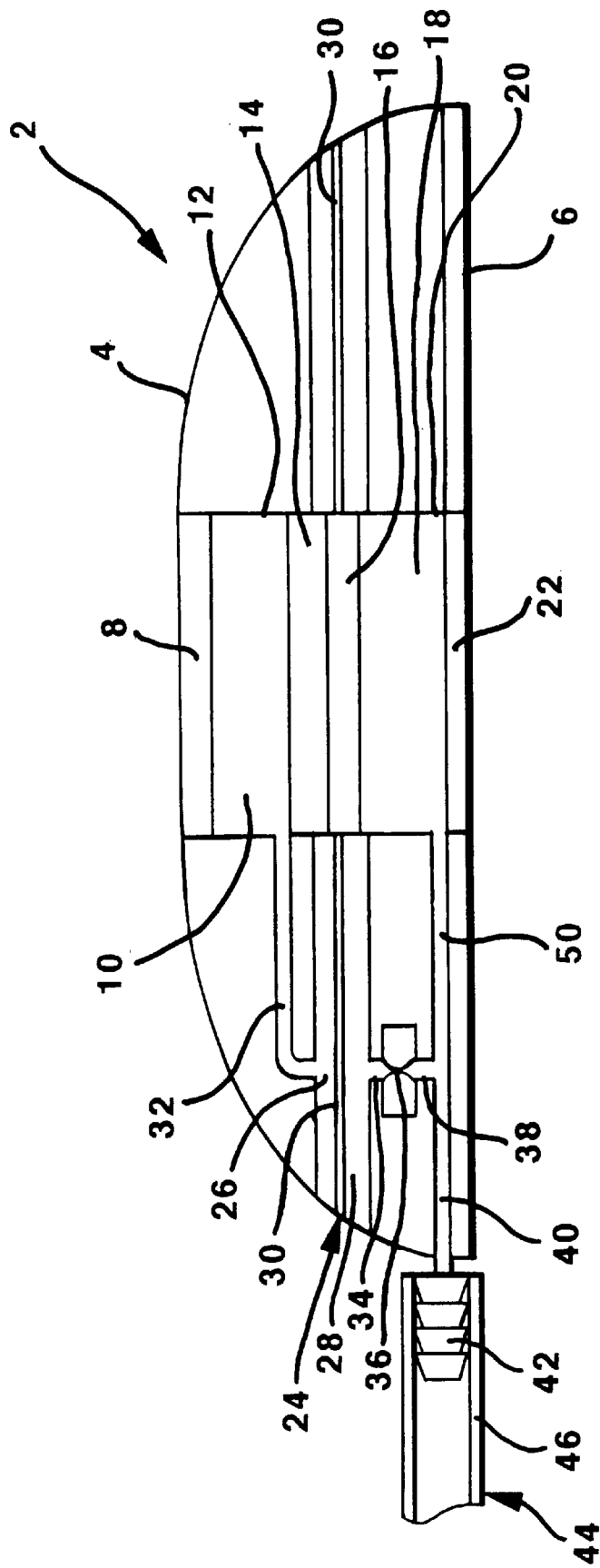
FIG. 2 is a side cross-sectional view of the access port of the present invention.
Figure 4B:
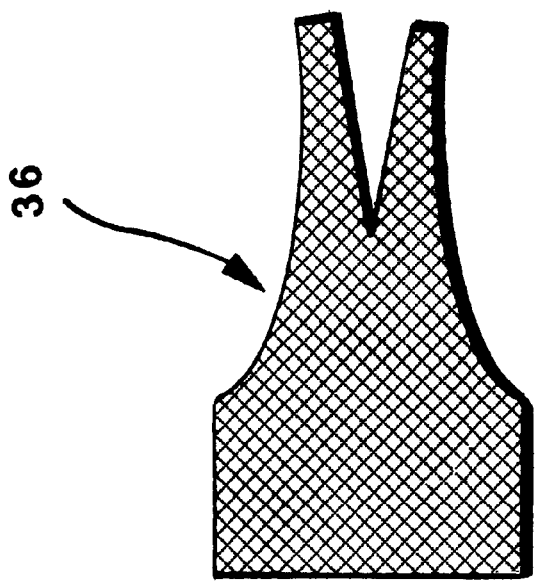
FIG. 4B is a side view of an open miter valve of one embodiment of the present invention.
Figure 4A:
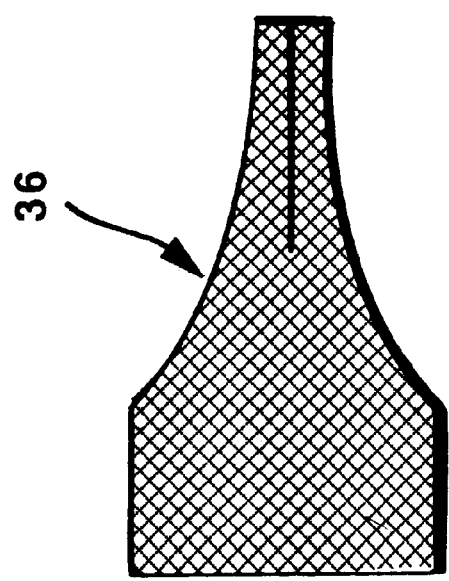
FIG. 4A is a side view of a closed miter valve of one embodiment of the present invention.
Figure 5:
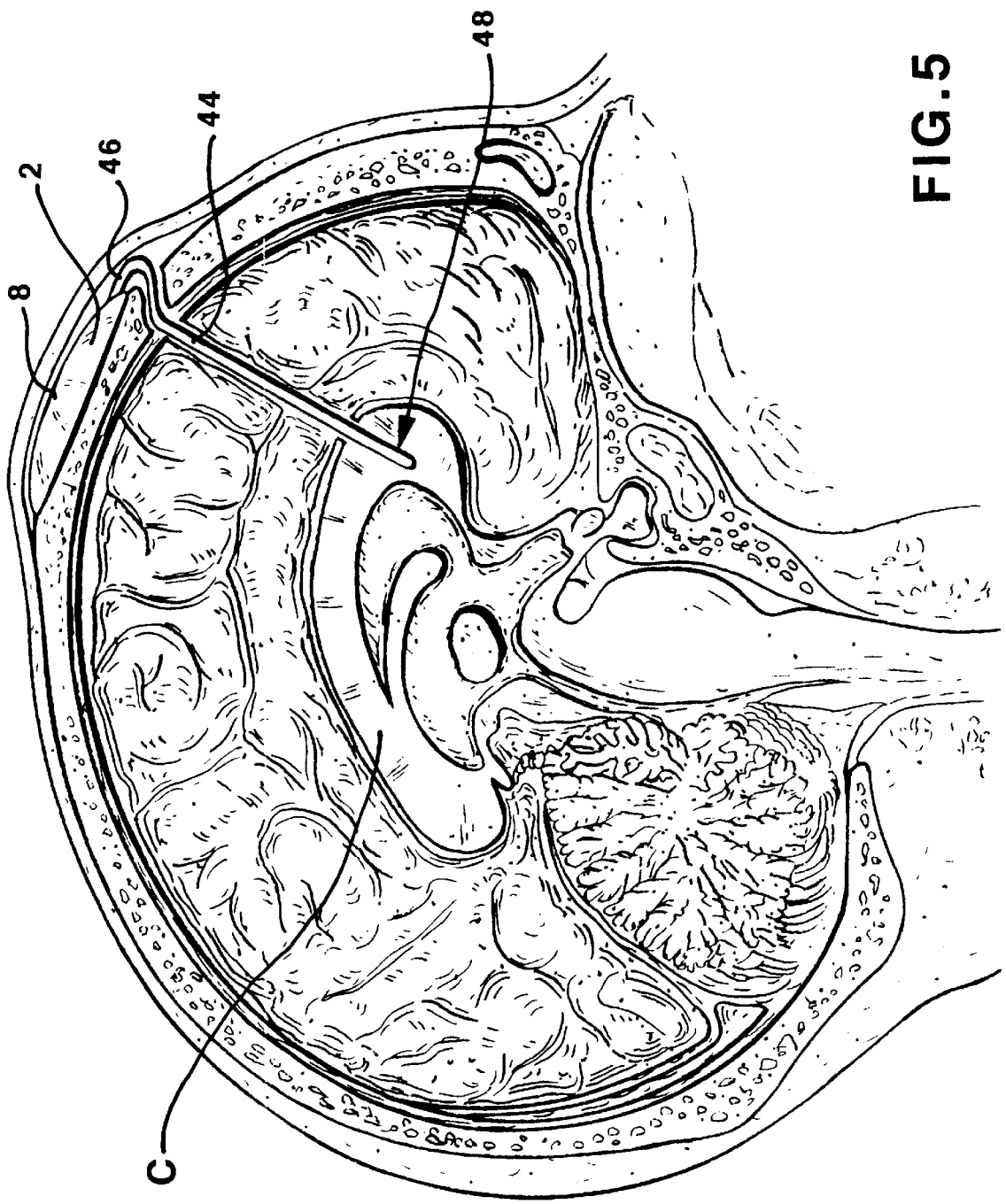
FIG. 5 is a side cross-sectional view of the access port of the present invention in place on a human head and attached to a catheter that is implanted in the ventricle of the brain.

An access port according to the present invention is shown in the Figures generally labeled 2. The access port 2 includes a generally dome shaped upper housing 4 and a disk shaped lower housing 6. Upper and lower housings 4, 6 are sealed at their periphery. Upper and lower housings 4, 6 are made of a body tolerant material such as titanium or a body compatible plastic such as silicone rubber. Housing 4 has a centrally located first septum 8. First septum 8 defines the upper boundary of a generally cylindrical first chamber 10. A generally cylindrical first wall 12 defines the walls of first chamber 10. First wall 12 is preferably made of a rigid material such as biocompatible polymer or titanium. A needle screen 14 is opposite first septum 8 and defines the lower boundary of first chamber 10.

Needle screen 14 prevents needles A having a diameter larger than a given diameter from passing therethrough while allowing needles B having diameters at or smaller than the given diameter to pass therethrough. In the preferred embodiment, needle screen 14 is a mesh screen made of wire. In the preferred embodiment, needle screen 14 allows needles B of 25 gauge or smaller to pass through while preventing needles A having diameters larger than 25 gauge from passing through.

A second septum 16 is immediately adjacent to and below needle screen 14. Second septum 16 defines the upper boundary of a generally cylindrical second chamber 18. First septum 8 and second septum 16 are preferably made of a resilient, pliable material such as silicone rubber that is self sealing if a needle is stuck through the septums and then removed. A generally cylindrical second wall 20 defines the walls of second chamber 18. Second wall 20 is also preferably made of a rigid material such as biocompatible polymer or titanium.

A needle stop 22 is opposite second septum 16 and defines the lower boundary of second chamber 18. Needle stop 22 prevents a needle passing through second chamber 18 from exiting second chamber 18 through the needle stop 22. Needle stop 22 is preferably made of a rigid, biocompatible polymer material. Needle stop 22 preferable rests on lower housing 6.

Access port 2 includes a torroidal shaped filter chamber 24 that surround first and second chambers 10, 18. Filter chamber 24 has an upper filter chamber 26 and a lower filter chamber 28. A filter 30 separates upper filter chamber 26 from lower filter chamber 28. Filter 30 is disk shaped and entirely spans filter chamber 24 so that any fluid in upper filter chamber 26 must pass through filter 30 to get to lower filter chamber 28. Filter 30 filters particulate matter, bacteria and other particles from drug passing through it. In the preferred embodiment, filter 30 has a pore size of about 0.22 micron.

An upper filter chamber conduit 32 exits first chamber 10 at the bottom of first chamber 10 near needle screen 14. Upper filter chamber conduit 32 is fluidly connected to upper filter chamber 26 so that drug leaving first chamber 10 passes into upper filter chamber 26.

A lower filter chamber conduit 34 is in fluid communication with lower filter chamber 28 and connects lower filter chamber 28 with a one-way valve 36. One-way valve 36 allows fluid to pass through it only in the direction of away from lower filter chamber 28. In the preferred embodiment, one-way valve 36 is a miter valve. In an alternate embodiment, one-way valve 36 is a ball and socket valve.

A first exit conduit 38 connects the outlet of one-way valve 36 with a catheter connector conduit 40 which is in fluid communication with a catheter connector 42. Catheter connector 42 is attached to housing 4 and allows a catheter 44 to be attached to access port 4. Catheter 44 has a proximal end 46 that is attached to access port 2 and a distal end 48 that discharges drug or other fluid at a selected site in a patient and allows CSF to be withdrawn therethrough. Catheter connector 42 is preferable a barbed connector that allows catheter 44 to be slid over its outer surface where the barbs retain catheter 44 in position.

A second exit conduit 50 fluidly connects second chamber 18 to catheter connector conduit 40 which is in fluid communication with catheter connector 42. Second exit conduit 50 is attached to second chamber 18 near needle stop 22.

To use the access port, a catheter 44 is surgically implanted so that the distal end 48 is located at a desired site in the brain or in the spinal column. The access port 2 is placed subcutaneously on the patient's cranium or on the patient's rib cage. The proximal end 46 of catheter 44 is attached to the catheter connector 42.

Figure 6:
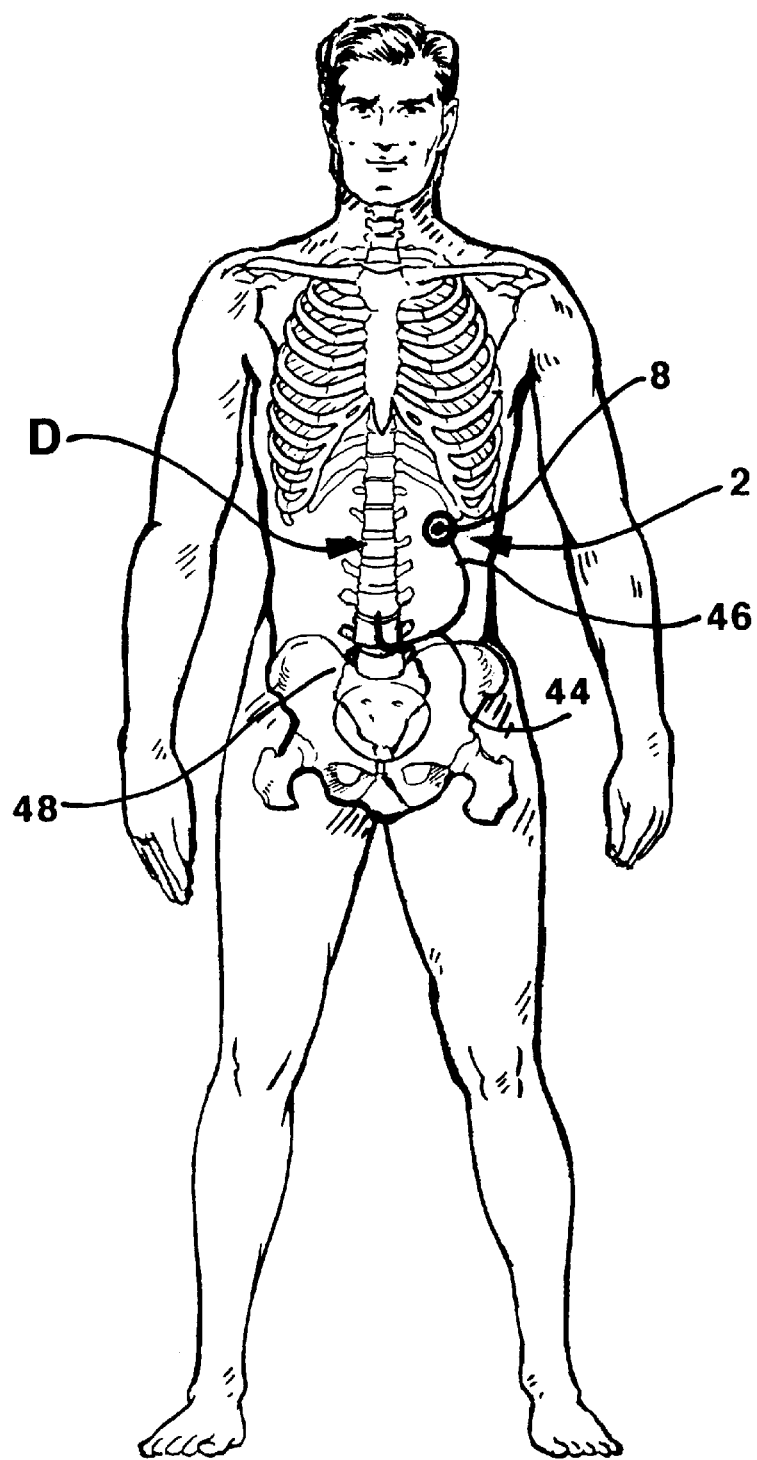
FIG. 6 is a side cross-sectional view of the access port of the present invention in place on a human rib-cage and attached to a catheter that is implanted in the intraspinal space.
Figure 7:
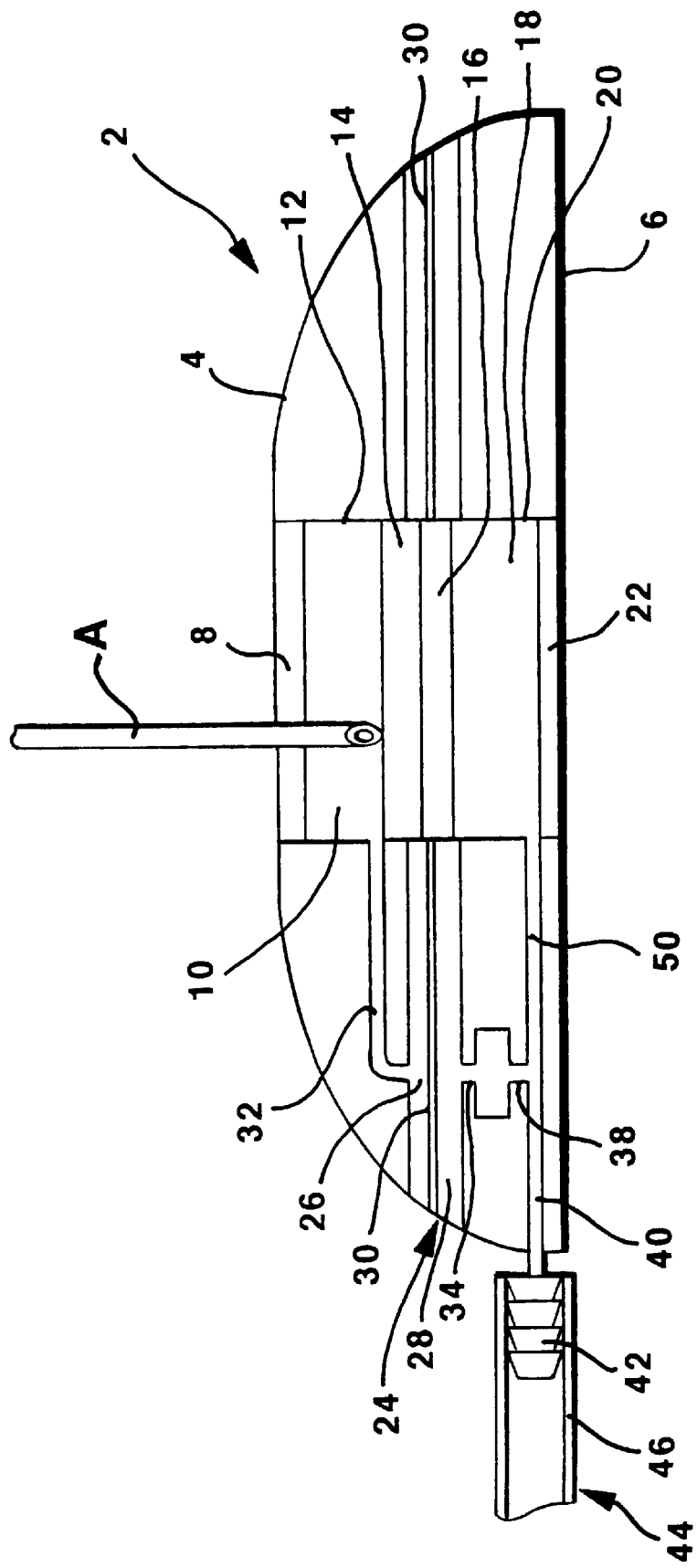
FIG. 7 is a side cross-sectional view of the access port of the present invention with a needle in the first chamber for administering drug to the patient.
Figure 8:
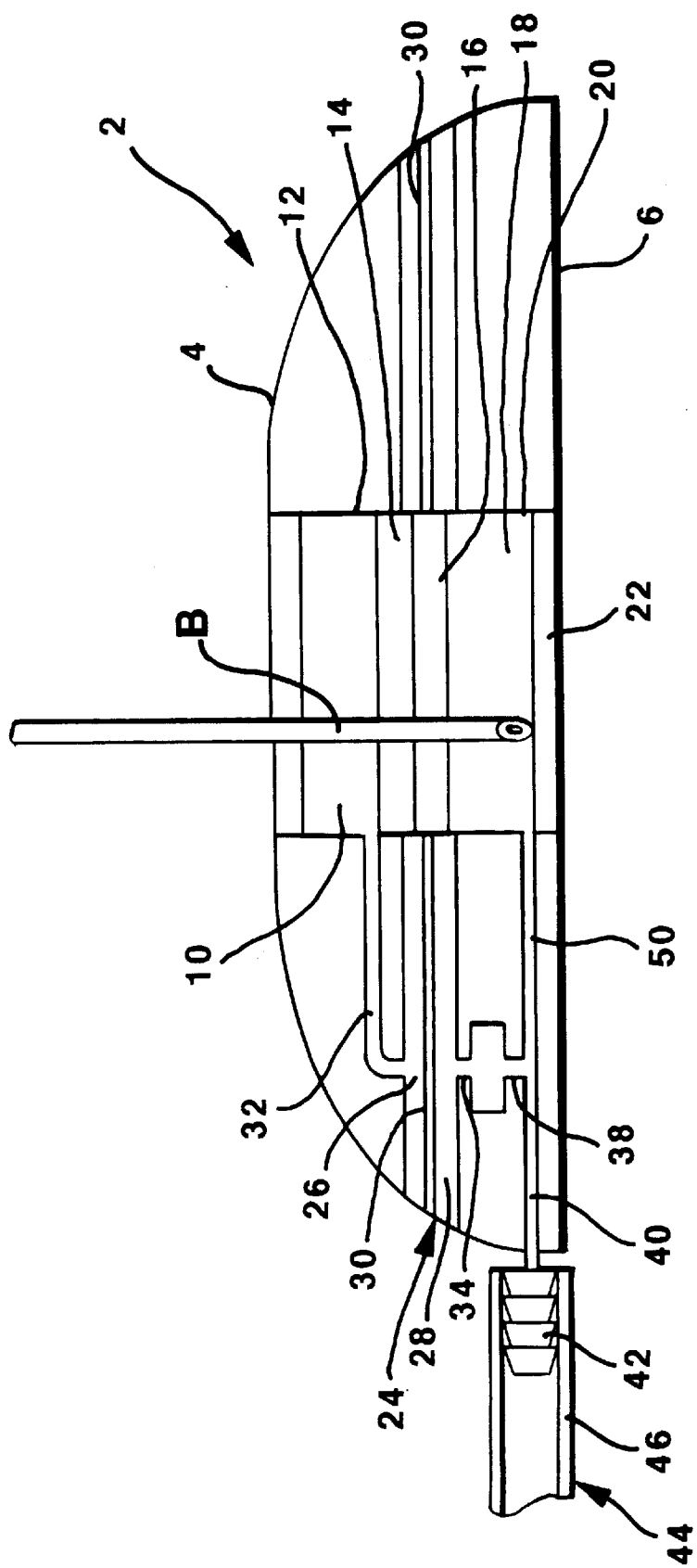
FIG. 8 is a side cross-sectional view of the access port of the present invention with a needle in the second chamber for removing a patient's CSF.

To use the access port 2, catheter 44 is surgically implanted in a patient's ventricle C in the brain (FIG. 6) or in a patient's intraspinal space D (FIG. 7). Access port 2 is placed cranially if catheter 44 is placed in a patient's ventricle C or on a patient's ribs if the catheter 44 is placed in the patient's intraspinal space D. In either case, access port 2 is placed subcutaneously and held in position by sutures. Catheter 44 is connected to access port 2 by sliding the proximal end 46 of catheter 44 over catheter connector 42.

To administer drug to a patient, a syringe with a needle A having a diameter larger than 25 gauge is filled with the desired amount of drug. The needle A is then passed through the patient's skin, through the first septum 8 and into the first chamber 10. Needle screen 14 and first wall 12 prevents the needle A from passing out of first chamber 10.

The drug is then expelled from the syringe through the needle A into the first chamber 10. The drug exits the first chamber 10 through the upper filter chamber conduit 32 where it passes to the upper filter chamber 26. The drug passes through filter 30 into lower filter chamber 28. From lower filter chamber 28, the drug, now filtered, passes into lower filter chamber conduit 34 and on to one-way valve 36. Because one-way valve 36 is biased to allow fluid flow from the filter chamber 26 to the catheter connector 42, the drug passes through one-way valve 36 and enters first exit conduit 38 where it passes to catheter connector conduit 40. The drug then passes to catheter connector 42 where it enters catheter 44 to be delivered to the patient.

Should the health care provider inadvertently try to withdraw fluid from first chamber 10, one-way valve 36 will prevent fluid from moving up through the lower filter chamber conduit 34, filter chamber 24 and upper filter chamber conduit 32 to replace fluid removed through the needle. Consequently, it will be very difficult if not impossible to remove fluid from the first chamber 10 through the needle A. As a result, it will be virtually impossible for CSF to move past one-way valve 36 into contact with filter 24. Therefore, the CSF will not pass through filter 24 and thereby clog filter 24.

To sample CSF, a syringe having a needle B with a diameter equal to or smaller than that required to pass through needle screen 14 is used. In the preferred embodiment, the needle B will have a diameter equal to or smaller than 25 gauge. The needle B is passed through the patient's skin and through the first septum 8 into the first chamber 10. The needle B is passed farther into contact with and through the needle screen 14 into second septum 16. The needle B then continues through the second septum 16 into the second chamber 18. The inside wall 20 and needle stop 22 prevent the needle B from passing out of the second chamber 18.

Second chamber 18 is in direct fluid communication with catheter 44 through second exit conduit 46 and catheter connector conduit 40. Catheter 44 is, in turn, in fluid communication with the patient's CSF. Fluid is withdrawn from second chamber 18 through the needle B. After a sufficient amount of fluid representing the volume of fluid in the catheter 44, the catheter connector conduit 40 and the second exit conduit 46 is withdrawn, CSF from the patient is withdrawn through the needle B.

The invention has been described in connection with particular embodiments. It is to be understood that the description given herein has been given for the purpose of illustrating the invention and the specific details of the invention given herein are not intended to limit the invention. For example, specific sizes of holes in the needle screen 14 and the pore sizes of the filter 24 have been given. In addition, specific geometric configurations of the first chamber 12, second chamber 18 and filter 24 have been given. These merely illustrate the preferred embodiments of the invention and are not intended to be limiting. In particular, other configurations of the first chamber 12 and the second chamber 18 may also fall within the invention including the first and second chambers 12, 18 being in a side by side configuration. In this alternate embodiment, first and second chambers 12, 18 may be accessed by needles A, B individually. That is, second chamber 18 may be accessed by a needle B without having needle B first pass through first chamber 12. In this embodiment, septums 8, 16 are each accessible from the outer surface of upper housing 4.

It is clear that improvements and modifications to the description given herein will occur to those skilled in the art and will still fall within the scope of the following claims.

What is claimed is:

1. An access port comprising:
   a housing having a first and a second chamber;
   a first septum defining a boundary of the first chamber, the first septum being accessible through the housing;
   a second septum defining a boundary of the second chamber;
   a catheter connector for connecting a catheter to the access port;
   a catheter connector conduit in fluid communication with the catheter connector;
   a first fluid pathway fluidly connecting the first chamber and the catheter connector conduit;
   a filter interdisposed along the first fluid pathway so that fluid passing along the first fluid pathway from the first chamber to the catheter connector conduit must pass through the filter;
   a one-way valve interdisposed along the first fluid pathway between the catheter connector conduit and the first chamber, the one-way valve allowing fluid to pass therethrough only in the direction toward the catheter connector conduit; and
   a second fluid pathway fluidly connecting the second chamber and the catheter connector conduit.

2. The access port of claim 1 wherein the first chamber is generally above the second chamber.

3. The access port of claim 2 wherein the second septum is accessible to a needle passing through the first chamber and a needle screen.

4. The access port of claim 3 further comprising a needle screen between the first and second chamber so that a needle passing from the first chamber to the second chamber must pass through the needle screen.

5. The access port of claim 4 wherein the needle screen comprises a mesh screen that allows needles of a certain diameter or smaller to pass through the mesh screen while preventing needles having a diameter larger than the certain diameter to pass through the wire screen.

6. The access port of claim 2 further comprising a needle stop preventing a needle entering the second chamber from exiting the second chamber.

7. The access port of claim 6 wherein the needle stop defines the lower boundary of the second chamber.

8. The access port of claim 6 wherein the needle stop is located across the second chamber opposite the second septum.

9. The access port of claim 1 further comprising a needle stop preventing a needle entering the second chamber from exiting the second chamber.

10. The access port of claim 1 wherein the filter has a pore size of about 0.22 micron.

11. An access port comprising:
    a housing having an upper surface, and a first and a second chamber;
    a first septum located at the upper surface of the housing, the first septum defining an upper boundary of the first chamber;
    a needle screen located opposite the first septum, the needle stop defining the lower boundary of the first chamber, the needle screen comprised of a mesh screen that allows needles of a certain diameter or smaller to pass through the mesh screen while preventing needles having a diameter larger than the certain diameter to pass through the wire screen;
    a second septum located immediately adjacent to and below the needle screen, the second septum defining the upper boundary of the second chamber;
    a needle stop located opposite second septum and defining the lower boundary of the second chamber;
    a catheter connector;
    a catheter connector conduit in fluid communication with the catheter connector;
    a first fluid pathway fluidly connecting the first chamber and the catheter connector conduit;
    a filter interdisposed along the first fluid pathway so that fluid passing along the first fluid pathway must pass through the filter;
    a one-way valve interdisposed along the first fluid pathway between the catheter connector conduit and the filter, the one-way valve allowing fluid to pass therethrough only in the direction toward the catheter connector conduit; and
    a second fluid pathway fluidly connecting the second chamber and the catheter connector conduit.

12. The access port of claim 11 wherein the filter has a pore size of about 0.22 micron.

13. An access port comprising:
    a housing having an upper surface, and a first and a second chamber;

first resealable means, located at the upper surface of the housing, for defining an upper boundary of the first chamber;

means, located opposite the first resealable means, for defining the lower boundary of the first chamber and for allowing needles of a certain diameter or smaller to pass therethrough while preventing needles having a diameter larger than the certain diameter from passing therethrough;

a second resealable means, located immediately adjacent to and below the means for defining the lower boundary of the first chamber, for defining the upper boundary of the second chamber;

means for defining the lower boundary of the second chamber;

means for connecting the access port to a catheter;

means for connecting the first chamber to the means for connecting the access port to a catheter including:

means, interdisposed along the means for connecting the first chamber to the means for connecting the access port to a catheter, for filtering fluid passing along the means for connecting the first chamber to the means for connecting the access port to a catheter, whereby such fluid must pass through the mean for filtering, and means for allowing fluid to pass along the means for connecting the first chamber to the means for connecting the access port to a catheter only in the direction toward the means for connecting the access port to a catheter;

means for connecting the second chamber to the means for connecting the access port to a catheter.

14. The access port of claim 13 wherein the first resealable means comprises a septum.

15. The access port of claim 13 wherein the means for defining the lower boundary of the first chamber comprises a needle screen.

16. The access port of claim 13 wherein the second resealable means comprises a septum.

17. The access port of claim 13 wherein the means for defining the lower boundary of the second chamber comprises a needle stop.

18. The access port of claim 13 wherein the means for connecting the access port to a catheter comprises a catheter connector.

19. The access port of claim 13 wherein the means for filtering includes a filter chamber.

20. The access port of claim 19 wherein the filter chamber surrounds the first and second chambers.

21. The access port of claim 19 wherein the filter chamber has an upper filter chamber and a lower filter chamber and a filter separating the upper filter chamber from the lower filter chamber.

22. The access port of claim 21 wherein the filter is disk shaped.

23. The access port of claim 21 wherein the filter has a pore size of about 0.22 micron.

24. The access port of claim 23 wherein the means for allowing fluid to pass along the means for connecting the first chamber to the means for connecting the access port to a catheter only in the direction toward the means for connecting the access port to a catheter comprises a one-way valve.

25. The access port of claim 24 wherein the one-way valve is a miter valve.

26. The access port of claim 24 wherein the one-way valve is a ball and socket valve.

* * * * *